United States Patent
Larson et al.

(10) Patent No.: US 6,868,346 B2
(45) Date of Patent: Mar. 15, 2005

(54) MINUTE VENTILATION SENSOR WITH AUTOMATIC HIGH PASS FILTER ADJUSTMENT

(75) Inventors: Dennis E. Larson, White Bear Township, MN (US); Douglas R. Daum, Oakdale, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 7 days.

(21) Appl. No.: 10/306,889

(22) Filed: Nov. 27, 2002

(65) Prior Publication Data

US 2004/0102908 A1 May 27, 2004

(51) Int. Cl.[7] ............................................... G01F 1/00
(52) U.S. Cl. ....................................................... 702/45
(58) Field of Search .............................. 702/45, 65, 75, 702/116, 182, 183, 189, 190; 607/17, 20, 28, 62

(56) References Cited

U.S. PATENT DOCUMENTS

| 4,901,725 A | 2/1990 | Nappholz et al. ............. 607/17 |
|---|---|---|
| 5,174,286 A | 12/1992 | Chirife ......................... 607/11 |
| 5,179,946 A | 1/1993 | Weiss ............................. 607/4 |
| 5,318,597 A | 6/1994 | Hauck et al. .................. 607/20 |
| 5,490,323 A | 2/1996 | Thacker et al. ............... 29/625 |
| 5,522,860 A | 6/1996 | Molin et al. .................. 607/20 |
| 5,722,997 A | 3/1998 | Nedungadi et al. ........... 607/28 |
| 5,817,135 A | 10/1998 | Cooper et al. ................ 607/17 |
| 5,824,029 A | 10/1998 | Weijand et al. ............. 607/122 |
| 6,044,294 A | 3/2000 | Mortazavi et al. .......... 600/547 |
| 6,076,015 A * | 6/2000 | Hartley et al. ................ 607/20 |
| 6,161,042 A * | 12/2000 | Hartley et al. ................ 607/20 |
| 6,463,326 B1 * | 10/2002 | Hartley et al. ................ 607/20 |
| 2003/0105499 A1 * | 6/2003 | Hartley et al. ................ 607/17 |
| 2004/0049237 A1 | 3/2004 | Larson et al. ................. 607/17 |

* cited by examiner

*Primary Examiner*—Michael Nghiem
(74) *Attorney, Agent, or Firm*—Schwegman, Lundberg, Woessner & Kluth, P.A.

(57) ABSTRACT

A minute ventilation sensing device in which transthoracic impedance is measured to generate an impedance signal from which a ventilation signal is derived, where the ventilation signal is proportional to minute ventilation. An adaptive high pass filter is used to filter the impedance signal into a ventilation band. The pole frequency of the high pass filter is adjusted in accordance with changes in a calculated signal variation parameter.

20 Claims, 8 Drawing Sheets

MINUTE VENTILATION SENSOR WITH AUTOMATIC HIGH PASS FILTER ADJUSTMENT

FIELD OF THE INVENTION

This invention pertains to implantable medical devices such as cardiac pacemakers. In particular, the invention relates to a device and method for improved sensing of physiological variables by impedance measurements.

BACKGROUND

Implantable medical devices are commonplace today for treating cardiac dysfunction. Cardiac pacemakers, for example, are implantable medical devices that replace or supplement a heart's compromised ability to pace itself (i.e., bradycardia) due to chronotropic incompetence or a conduction system defect by delivering electrical pacing pulses to the heart. Pacemakers can deliver pacing pulses asynchronously at a fixed rate or synchronously in a manner that depends upon sensed intrinsic beats. Most pacemakers today are operated in some sort of synchronous mode where the pacing pulses are delivered upon the expiration of escape intervals that are reset by sensed intrinsic depolarizations of the heart. The pacing rate is then determined by the programmed escape intervals of the pacemaker and is referred to as the lower rate limit or LRL in the case of ventricular pacing.

In chronotropically competent patients in need of ventricular pacing, atrial triggered modes where ventricular pacing is controlled by sensed atrial beats are desirable because they allow the pacing to track the physiologically normal atrial rhythm, which then causes cardiac output to be responsive to the metabolic needs of the body. Atrial triggered modes are contraindicated, however, in patients prone to atrial fibrillation or flutter or in whom a reliable atrial sense cannot be obtained. In pacemaker patients who are chronotropically incompetent (e.g., sinus node dysfunction) or in whom atrial triggered modes are contraindicated, the heart rate is dictated solely by the pacing rate of the pacemaker in the absence of faster intrinsic cardiac activity.

Pacing the heart either asynchronously at a fixed rate or synchronously at a rate determined by the LRL setting of the pacemaker, however, does not allow the heart rate to increase with increased metabolic demand. If the heart is paced at a constant rate, severe limitations are imposed upon the patient with respect to lifestyle and activities. It is to overcome these limitations and improve the quality of life of such patients that rate-adaptive pacemakers have been developed. Such pacemakers are rate-controlled in accordance with a measured physiological variable that corresponds to exertion level and is indirectly reflective of the body's metabolic rate. The measured exertion level is mapped to a particular target heart rate by a specified rate-response factor, the inverse of the target rate then being used as the escape interval for atrial or ventricular pacing. Minute ventilation is the amount of air breathed by a subject over a minute or other specified period of time and can be computed as the product of respiratory rate and tidal volume. Minute ventilation is a good indicator of the rate of oxygen consumption and hence is one of the best measurements of a patient's exertion level.

Rate-adaptive pacemakers may use an impedance technique for measuring minute ventilation. The blood and body fluids within the thoracic cavity constitute a volume conductor, and the electrical impedance between any two points in the thoracic cavity is dependent upon the volume of blood and/or air between the two points. The impedance can be measured by impressing a constant current field within the cavity and then measuring the potential difference between the two points. By appropriate placement of voltage sensing electrodes, an impedance signal can be produced that corresponds to the movement of air into and out of the lungs as a subject breathes. Thus, in order to measure minute ventilation, a constant excitation current may be made to flow between two excitation current electrodes located within the thoracic cavity, and the voltage difference between two appropriately located voltage sense electrodes in the cavity is measured. The resulting impedance signal can then be filtered to derive a ventilation signal that is proportional to the subject's ventilation. Breathing patterns and the amplitudes of the ventilation signal vary, however, which places demands on the dynamic range of the minute ventilation sensor.

SUMMARY

The present invention relates to a technique for increasing the accuracy of a minute ventilation sensor across a greater dynamic range of respiration amplitude variations. In one embodiment, a minute ventilation sensor includes electrodes for generating an impedance signal corresponding to a potential difference between two points in the thoracic cavity when excitation current is applied, sampling circuitry for sampling the impedance signal, circuitry for filtering the impedance signal samples into a ventilation band to thereby generate a ventilation signal, and circuitry for deriving a signal proportional to minute ventilation from the ventilation signal. The filtering circuitry includes a high pass frequency with a variable pole frequency for removing the DC component of the impedance signal samples. The device also includes circuitry for calculating a signal variation parameter from a set of impedance signal samples and circuitry for adjusting the frequency response of the high pass filter in a manner that tends to compensate for changes in the calculated signal variation parameter as compared with a specified nominal value.

DETAILED DESCRIPTION

The present invention is a device and method for processing a transthoracic impedance signal in order to perform minute ventilation sensing. It may be applied in any type of apparatus utilizing impedance measurement as a technique for sensing minute ventilation, including cardiac pacemakers. The invention may be incorporated into a number of minute ventilation sensing systems, a particular one of which is described in U.S. Pat. No. 6,161,042 (referred to herein as the '042 patent), assigned to the assignee of the present application and hereby incorporated by reference in its entirety.

1. Minute Ventilation Sensing by Impedance Measurement

Figure 1:
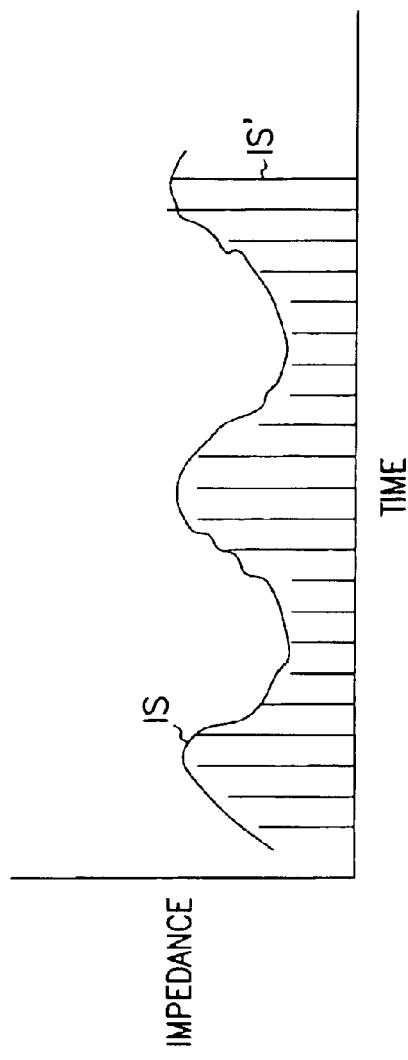
FIG. 1 shows an example of an impedance signal.

As noted above, the electrical impedance of a conductive path between two points that includes part of the thoracic cavity varies in accordance with a subject's respiration. If the voltage between two voltage sense electrodes in the thoracic cavity were measured while a constant excitation current flows between two current source electrodes, a voltage signal corresponding to the impedance between the sense electrodes would be produced. FIG. 1 shows such a transthoracic impedance signal IS that represents the time-varying impedance between the two sense electrodes while the subject breathes as would be generated by a continuous (i.e., DC) constant excitation current. However, it is preferable to inject the excitation current in the form of a pulse train with narrow pulse-widths in order to conserve battery energy. The impedance signal produced at the voltage sense electrodes is then a pulse train at the excitation frequency that is amplitude-modulated by the impedance signal IS. The resulting signal can also be regarded as a discrete-time impedance signal IS' with each signal value representing samples of the continuous impedance signal IS taken at a sampling rate equal to the excitation frequency.

Before deriving the minute ventilation, the impedance signal is filtered to remove both low and high frequency components. The impedance signal thus filtered will be referred to as the ventilation signal. The low frequency components of the impedance signal include both a zero frequency or DC voltage that represents the impedance at full expiration and lower frequency voltages that represent impedance changes due to the slow changes in residual volume of the lungs that occur as the subject alternates between deep and shallow breathing. The high frequency components of the impedance signal include both voltages representing impedance changes resulting from the changes in ventricular blood volume as the heart beats and voltages caused by additional current fields produced from external noise sources. These components can be removed with a bandpass filter or a combination of low-pass and high-pass filtering. Exemplary lower and upper cutoff frequencies for such filtering could be on the order of 0.1 and 1 Hz, respectively, which thus define a ventilation band in which the ventilation signal is found. After filtering the impedance signal to remove the unwanted frequency components, the resulting ventilation signal is directly reflective of the movement of air into and out of the lungs. The minute ventilation can then be derived from the ventilation signal by a number of different methods. For example, the signal can be filtered to derive both a respiratory rate and an average tidal volume, the product of which is the minute ventilation. Alternatively, successive peak-to-peak transitions of the signal, each of which represents the quantity of air inspired during a breath, can be summed over a specified period of time to result in a minute ventilation value.

Figure 2:
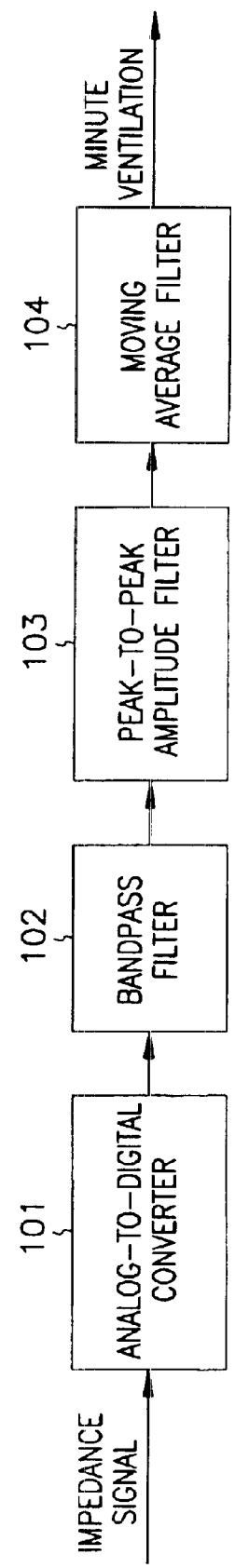
FIG. 2 is a diagram of exemplary functional circuitry for deriving minute ventilation from an impedance signal.

The impedance signal can be processed in either the analog or digital domain or with a combination of digital and analog processing in order to compute the minute ventilation. For example, the discrete time signal IS' generated by the voltage sense electrodes when excitatory current pulses are output can be low-pass filtered to remove the pulse train carrier waveform. The resulting analog waveform can then be further filtered to derive the ventilation signal as described above. The additional filtering can be performed in the analog domain, or the analog signal can be sampled and converted into a digital signal that can be processed in the digital domain. Alternatively, the values of the discrete time signal IS', which correspond to measurements of the voltage between the voltage sense electrodes during an excitation current pulse, can be digitized and processed entirely in the digital domain. FIG. 2 is a block diagram showing one example of how the impedance signal IS' may be further processed either in the analog or digital domain to derive the minute ventilation. A digital bandpass filter 102 (or, equivalently, a combination of low and high pass filters) filters the impedance signal IS' to generate the ventilation signal VS. A peak-to-peak transition filter 103 then derives successive amplitudes of peak-to-peak transitions of the VS waveform that represent inspirations. Each such peak-to-peak transition amplitude is proportional to the tidal volume during a single breath. The successive peak-to-peak transition amplitudes are then filtered by a moving average filter 104 with a specified averaging period to derive a signal proportional to the minute ventilation.

2. Exemplary System Description

Figure 3:
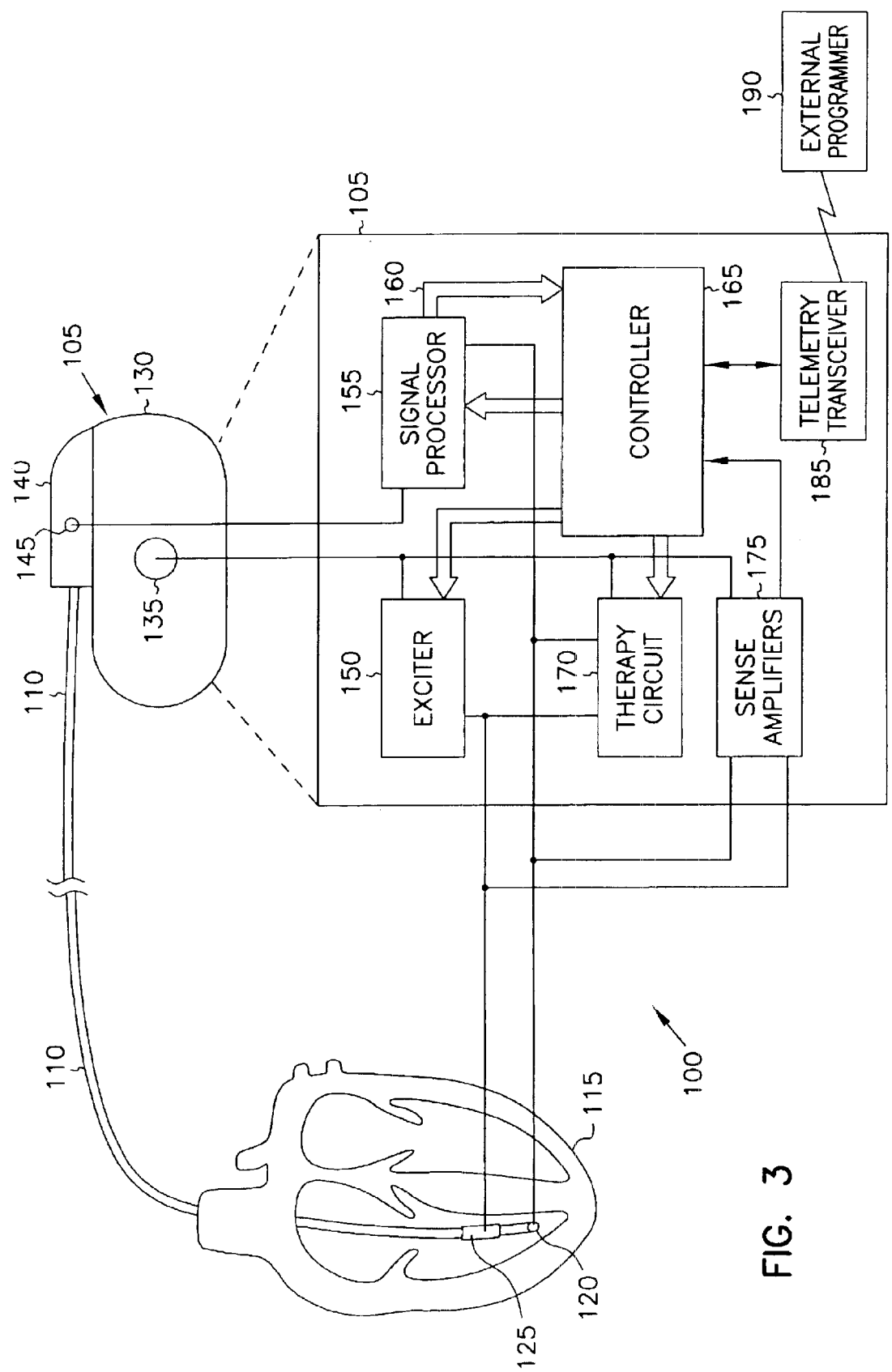
FIG. 3 illustrates an exemplary cardiac rhythm management device according to the present invention.

FIG. 3 is a schematic/block diagram illustrating one embodiment of a cardiac rhythm management system 100 according to the present invention. The illustrated system includes a cardiac rhythm management device 105 and a lead 110 for communicating voltage signals between device 105 and electrodes disposed near or in the heart 115. Device 105 may be, for example, a pacemaker capable of delivering bradycardia pacing and, in addition, anti-tachycardia pacing, cardioversion/defibrillation, drug deliver or other therapy to heart 115. The device 105 includes a controller 165 which is preferably a processing element such as a microprocessor. The controller could be implemented by other types of logic circuitry (e.g., discrete components or programmable logic arrays) using a state machine type of design, but a microprocessor-based system is preferable. As used herein, the term "circuitry" should be taken to refer to either discrete circuitry configured to perform particular functions or to the code executable by a microprocessor. The controller controls the delivery of stimulation to the heart via therapy circuit 170, processes signals reflecting cardiac activity from sense amplifiers 175, and processes impedance measurement signals from signal processor 155. As described above, the impedance measurement signals are used to derive a minute ventilation signal that is used to modulate the pacing rate during bradycardia pacing. Also interfaced to the controller 165 is a telemetry transceiver 185 capable of communicating with an external programmer 190.

Cardiac rhythm management devices may be external to the patient but are usually implanted in a pectoral or abdominal region with one or more leads threaded through the upper venous system to reach the heart. FIG. 3 shows tip electrode 120 and ring electrode 125 separately coupled to device 105 via conductors within multiconductor lead 110. The device 105 includes a hermetically sealed housing 130, formed from a conductive metal, such as titanium. Housing 130 (also referred to as a "case" or "can") may be substantially covered over its entire surface by a suitable insulator, such as silicone rubber, except for at a window that forms a third electrode, referred to as a "case" or "can" electrode 135. A header 140 is mounted on housing 130 for receiving lead 110. The header may be formed of an insulative material, such as molded plastic and also includes a fourth electrode, referred to as indifferent electrode 145. A device may have one or multiple leads with electrodes disposed in the right atrium or ventricle or in a cardiac vein for sensing cardiac activity and/or delivering electrical stimulation to the heart. For example, the tip and ring electrodes may be used together by the therapy circuit 170 and/or sense amplifiers 175 for bipolar pacing/sensing of the heart or in combination with the case or indifferent electrode for unipolar pacing/ sensing. Of primary interest here, however, are electrodes used for delivering excitation current to the thorax and for sensing an impedance signal resulting from the current field. Such electrodes may be the same electrodes used for delivering therapy or may be separate electrodes.

Device 105 includes an exciter 150 for delivering excitation current between a selected pair of excitation current electrodes. A current field is thus imposed in the thoracic cavity so that the potential difference between a selected pair of voltage sense electrodes, also located within the thoracic cavity, will be proportional to the impedance between the electrodes. In the example of FIG. 1, the excitation current electrodes are the ring electrode 125 and case electrode 135, shown as connected to the exciter 150. The voltage sense electrodes are the tip electrode 120 and the indifferent electrode 145, shown as electrically connected to the signal processor 155. Thus, in this embodiment, the excitation current electrodes are different from the voltage sense electrodes which advantageously reduces the magnitude of the baseline component of the transthoracic impedance signal, thereby increasing the relative contribution of the ventilation component of the transthoracic impedance signal, and increasing the signal-to-noise ratio (SNR). Alternatively, the same electrodes could be used for delivering the excitation current and sensing the voltage induced thereby. Other embodiments may use different combinations of these or other electrodes as the excitation current and voltage sensing electrodes.

Exciter and Excitation Current Waveform

Figure 4:
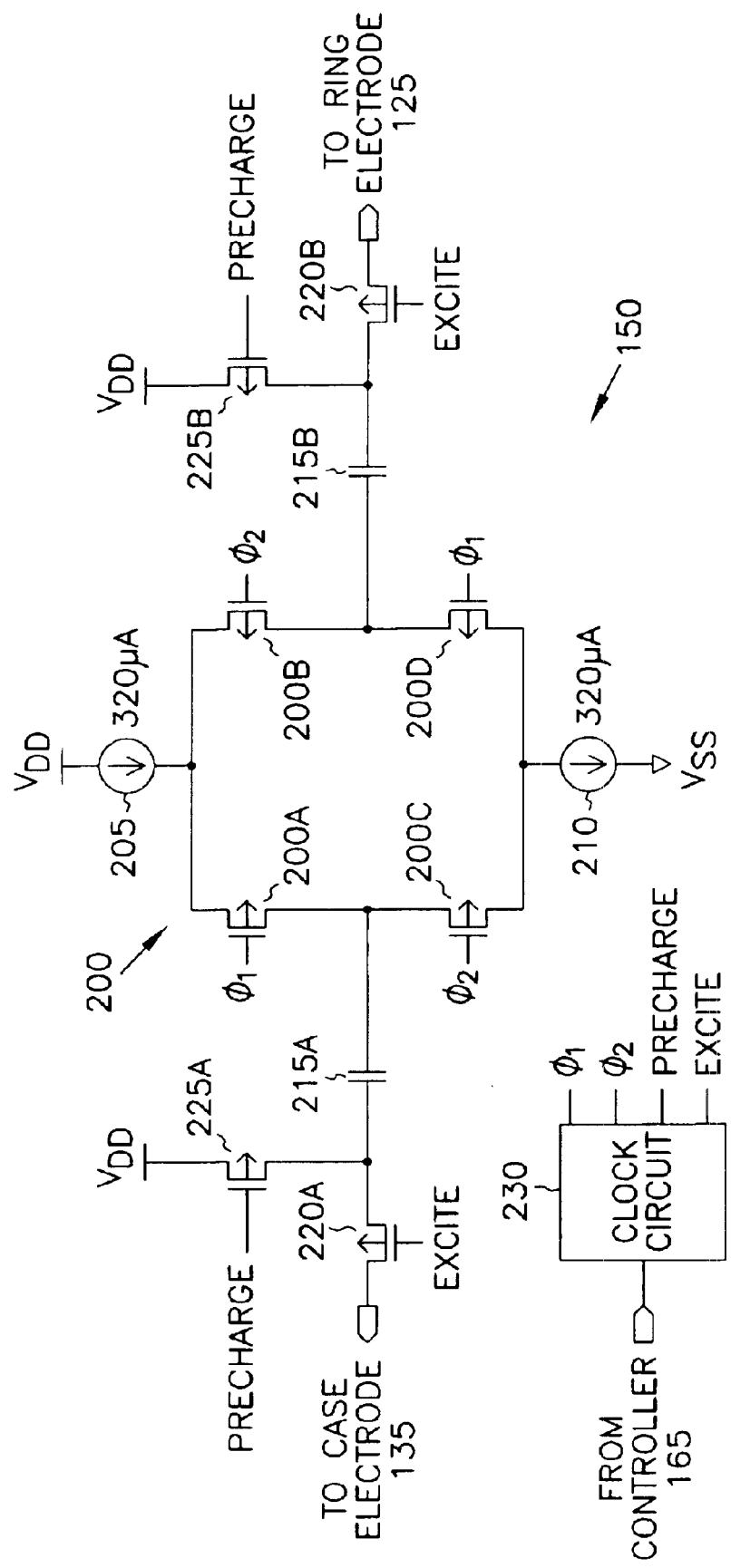
FIG. 4 is illustrates the components of an exemplary exciter for delivering electrical excitation current.

FIG. 4 is a schematic diagram illustrating one embodiment of particular elements included within exciter 150 for delivering excitation current in the form of a carrier waveform that is modulated by transthoracic impedance changes. A bridge switcher 200 includes switches 200A, 200B, 200C, and 200D that may be implemented as transistors, such as p-channel metal-oxide semiconductor (PMOS) field-effect transistors (FETs) or any other suitable switches. The exciter 150 also includes current source 205 and current sink 210, each of which may be implemented with transistors in a regulated cascode or other suitable configuration. Switcher 200 is electrically coupled to case electrode 135 and ring electrode 125 through respective dc blocking capacitors 215A and 215B and respective switches 220A and 220B (e.g., PMOS transistors). Switches 225A and 225B (e.g., PMOS transistors) precharge respective capacitors 215A and 215B. Exciter 150 also includes a clock circuit 230 that receives one or more control signals from controller 165 and provides signals to the control terminals of each of switches 200A–D, 220A–B, and 225A–B. The control signals from the controller 165 to the clock circuit cause the exciter to output a bipolar excitation waveform at a specified excitation frequency and for a specified duration. As explained below, in a preferred embodiment, the excitation waveform is output in the form of a strobe made up of a specified number of excitation current waveform cycles with each strobe repeated at a specified strobing frequency.

Figure 5:
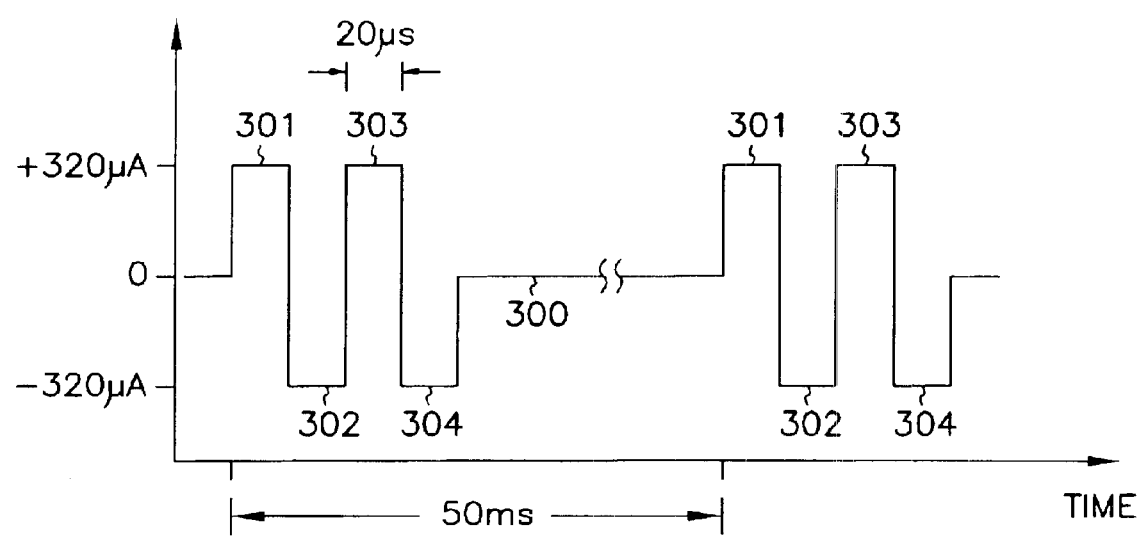
FIG. 5 illustrates a current waveform resulting from operation of an exciter according to one embodiment of the invention.

FIG. 5 illustrates an exemplary excitation current waveform 300 as may be generated by exciter 150 between case electrode 135 and ring electrode 125 in a particular embodiment. Waveform 300 is a multiphase stimulus that is a bipolar square wave strobe made up of four current pulses 301, 302, 303, and 304 in sequentially alternating polarity/ direction, each current pulse being a phase of the multiphase stimulus. In the embodiment illustrated in FIG. 5, pulses 301–304 form a square wave having a carrier frequency of approximately 25 kilohertz where each pulse has a duration of 20 microseconds. Also in this embodiment, the four pulse sequence 301–304 is repeated at a strobing frequency of approximately 20 Hertz (i.e., a 50 millisecond time interval). Other suitable durations of current pulses 301–304 could also be used to result in a different carrier frequency, and other suitable strobing frequencies could be used. As explained in more detail below, the voltage sense signal waveform may be sampled during each phase (i.e., during each current pulse 301, 302, 303, and 304) of a strobe so that the sampling rate is twice the excitation frequency. Other embodiments may employ a sampling rate that is differently related to the excitation frequency. The samples of each strobe are then filtered by a demodulator that computes a weighted average of the samples with specified filter coefficients. As explained below, due to the bipolar nature of the excitation current waveform, the demodulator has the effect of filtering out components of the voltage sense signal due to external fields while averaging the impedance signal component of the voltage sense signal. The demodulated voltage sense signal samples thus constitute samples of the impedance signal at a sampling rate equal to the strobing frequency. The strobing frequency should therefore be sufficiently high so as to provide adequate sampling of ventilation or other information carried by the transthoracic impedance signal contained within the voltage sense signal. Such ventilation information can appear at frequencies as high as approximately 1 Hertz, depending on the patient's breathing rate. The strobing frequency should also minimize aliasing of a "stroke volume" component of the impedance signal (i.e., a portion of the transthoracic impedance signal that varies along with the patient's heartbeat instead of the patient's breathing rate) and which can have frequencies as high as approximately 3 Hertz, depending on the patient's heart rate. In order to avoid aliasing the stroke volume component of the impedance signal into the ventilation band, the strobing frequency should be at least twice the highest frequency component expected to be in the impedance signal in accordance with the Nyquist criterion.

The amplitude of current pulses 301–304 is controlled by the controller 165 and is preferably set at some minimum value that provides enough excitation to obtain an adequate voltage response signal while minimizing current drain of the implanted device 105, thereby increasing its implanted longevity. The amplitude of the excitation current pulses should also be minimized in order to prevent unwanted cardiac stimulation and to prevent false sensing of the pulses by the sensing channels of the device where the current pulses are misinterpreted as cardiac activity. For example, in one embodiment, the amplitude of the current pulses 301–304 is selected to be approximately 320 microampere, but other current pulse amplitudes may also be employed. As explained below, the current pulse amplitude may be adjusted by the controller 165 in accordance with a detected noise level so as to maintain an adequate signal-to-noise ration.

Prior to each sequence of current pulses 301–304, dc blocking capacitors 215A–B are precharged by a bias circuit, such as by turning on switches 200A–D and 225A–B, with switches 220A–B being off. Current source 205 and current sink 210 establish the operating point of a terminal of each of dc blocking capacitors 215A–B that is coupled to switcher 200. After precharging, switches 225A–B are turned off. Next, pulse 301 is produced by turning on switches 200A, 200D, and 220A–B, such that current delivered by current source 205 leaves case electrode 135. The current returns through ring electrode 125, and is sunk by current sink 210. Next, pulse 302 is produced by turning on switches 200B–C and 220A–B, such that current delivered by current source 205 leaves ring electrode 125. The current returns through case electrode 135, and is sunk by current sink 210. Next, pulse 303 is produced by again turning on switches 200A, 200D, and 220A–B, such that current delivered by current source 205 leaves case electrode 135. The current returns through ring electrode 125, and is sunk by current sink 210. Next, pulse 304 is produced by again turning on switches 200B–C and 220A–B, such that current delivered by current source 205 leaves ring electrode 125. The current returns through case electrode 135, and is sunk by current sink 210. Switches 220A–B, 200A–D, and 225A–B are turned off until precharging for another four current pulse sequence 301–304, which is delivered approximately 50 milliseconds later in the embodiment illustrated in FIG. 5. Preferably, clock circuit 230 provides nonoverlapping control signals to switches 225A–B and switches 220A–B so that switches 225A–B are not turned on at the same time as switches 220A–B. This avoids any coupling of either of case electrode 135 and ring electrode 125 to the positive power supply voltage VDD.

Signal Processor

Figure 6A:
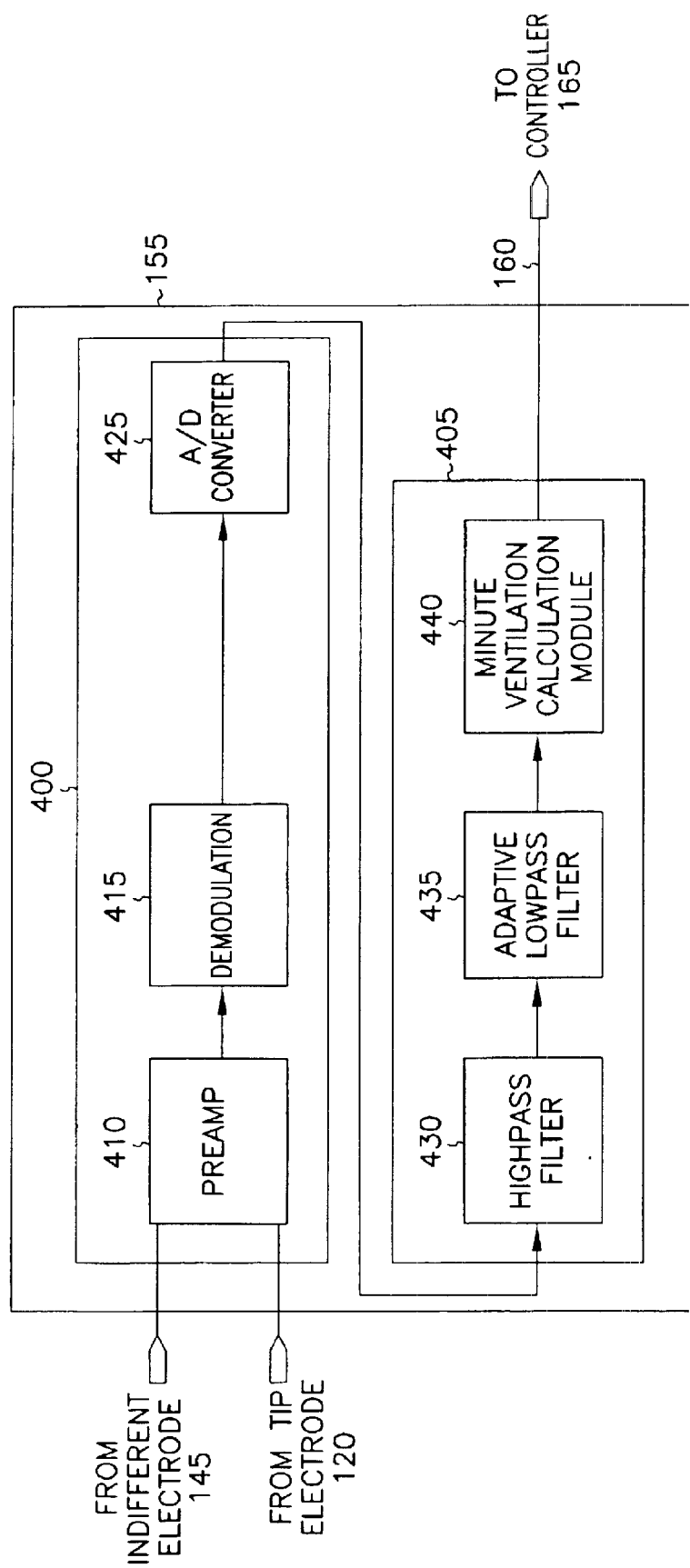
FIG. 6A is a block diagram illustrating one embodiment of a signal processor.

FIG. 6A is a block diagram illustrating one embodiment of portions of signal processor 155. Signal processor 155 includes analog signal processing circuit 400 and digital signal processing circuit 405. Inputs of a preamplifier 410 of analog signal processing circuit 400 are electrically coupled to each of indifferent electrode 145 and tip electrode 120 for receiving a voltage sense signal in response to the above-described stimuli provided by exciter 150. An exemplary preamplifier is described in detail in the '042 patent, particularly with reference to FIG. 5 of that document. Analog signal processing circuit 400 also includes demodulator 415 that samples the analog output of preamplifier 410 and provides an output signal received by analog-to-digital (A/D) converter 425. The digitized output signal from A/D converter is then processed by digital processing circuit 405 which includes high pass filter 430, low pass filter 435, and minute ventilation calculation module 440. The output signal from A/D converter 425 is input to high pass filter 430 and then to low pass filter 435. Minute ventilation calculation module 440 receives an output signal from low pass filter 435 and provides a calculated minute ventilation signal at node 160 to controller 165.

Figure 6B:
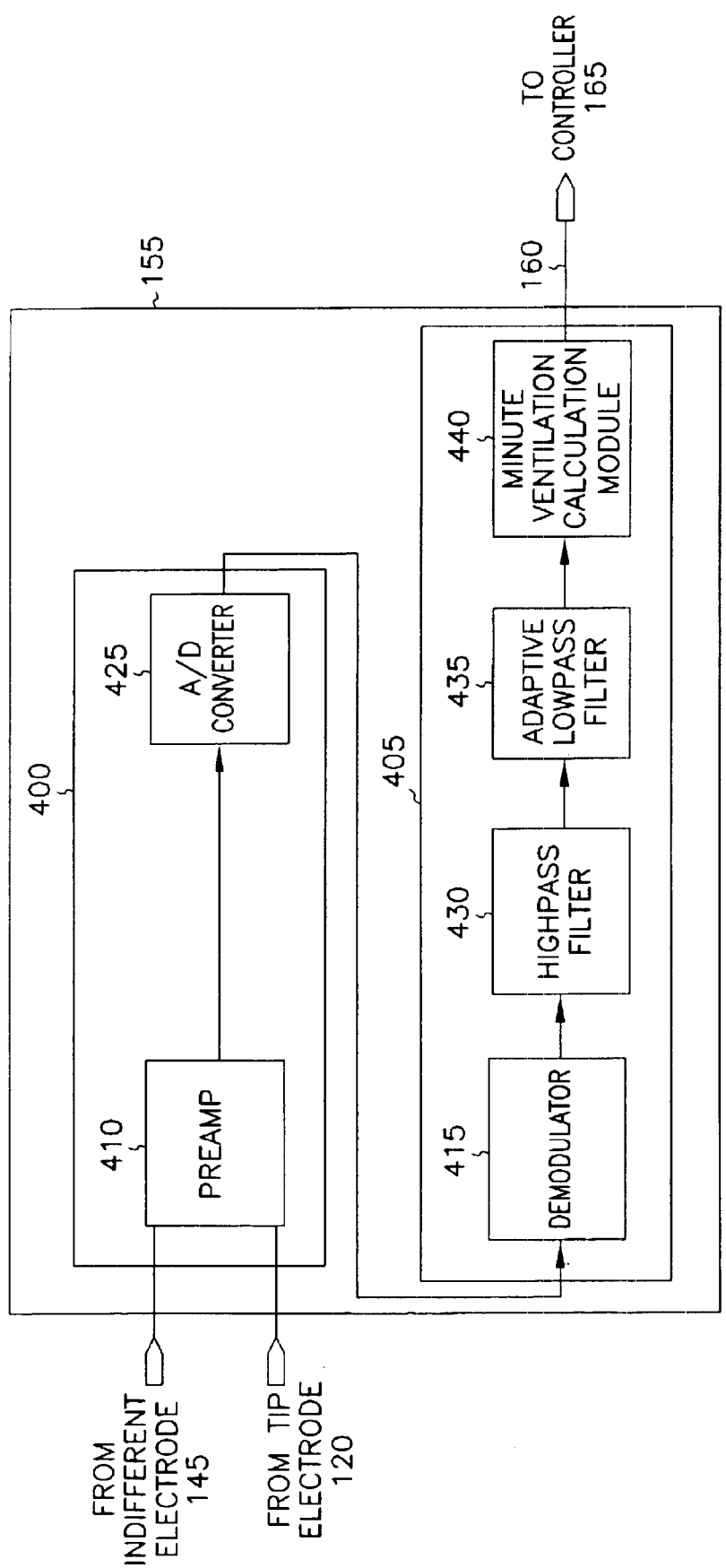
FIG. 6B is a block diagram illustrating an embodiment of a completely digital signal processor.

FIG. 6B shows another embodiment of the signal processor in which the analog processing circuit is made up of preamplifier 410 and A/D converter 425, with the functionality of the demodulator 415 being moved to the digital processing circuit. In this embodiment, the voltage sense signal is digitized immediately after preamplification, and the demodulator 415 is a digital filter. In either of the embodiments shown in FIG. 6A or 6B, the digital signal processing circuit 405 may be implemented as coded instructions executed by controller 165 or as separately implemented hardware portions dedicated to performing the digital signal processing tasks described below.

Demodulator

The demodulator portion of the signal processor removes the excitation current waveform from the voltage sense signal samples of each strobe by low-pass filtering of the voltage sense signal samples. As explained more fully below, a discrete-time low-pass filter will have the further advantageous effect of high-pass filtering external field noise from the voltage sense signals due to the bipolar nature of the excitation current waveform.

As shown in FIGS. 6A and 6B, the demodulator 415 may be implemented in either the digital or analog domain. In FIG. 6A, the analog demodulator 415 includes sampling circuitry for converting the output of the preamplifier into a discrete-time analog signal. In FIG. 6B, on the other hand, the analog-to-digital converter 425 includes circuitry for both sampling and digitizing the output of the preamplifier, the digitized voltage sense signal then being input to the digital demodulator 415. In either case, the sampling is synchronized to the excitation current waveform. Thus, referring to FIG. 5, the output of preamplifier 410 is sampled some time during each of current pulses 301–304. Demodulator 415 then combines these four samples into a single value using a weighted average to effect both low-pass filtering of the impedance signal and high-pass filtering of external field noise.

In one embodiment, the demodulator filter is a finite impulse responses filter that computes a weighted average of the strobe samples. The weighted average is formed by weighting the second and third samples, obtained from respective current pulses 302 and 303, by a factor of approximately 3.0 relative to the first and fourth samples, obtained from respective current pulses 301 and 304. A transfer function representing this embodiment of demodulator 415 is described in the z-domain as:

$$H(z) = K(z^{-3} - 3z^{-2} + 3z^{-1} - 1)$$

where K is a gain associated with the filtering. In a digital demodulator 415, the transfer function can be implemented directly as code. The transfer function can be implemented in one embodiment of an analog demodulator as a switched capacitor circuit that also performs a sampling function.

Figure 7:
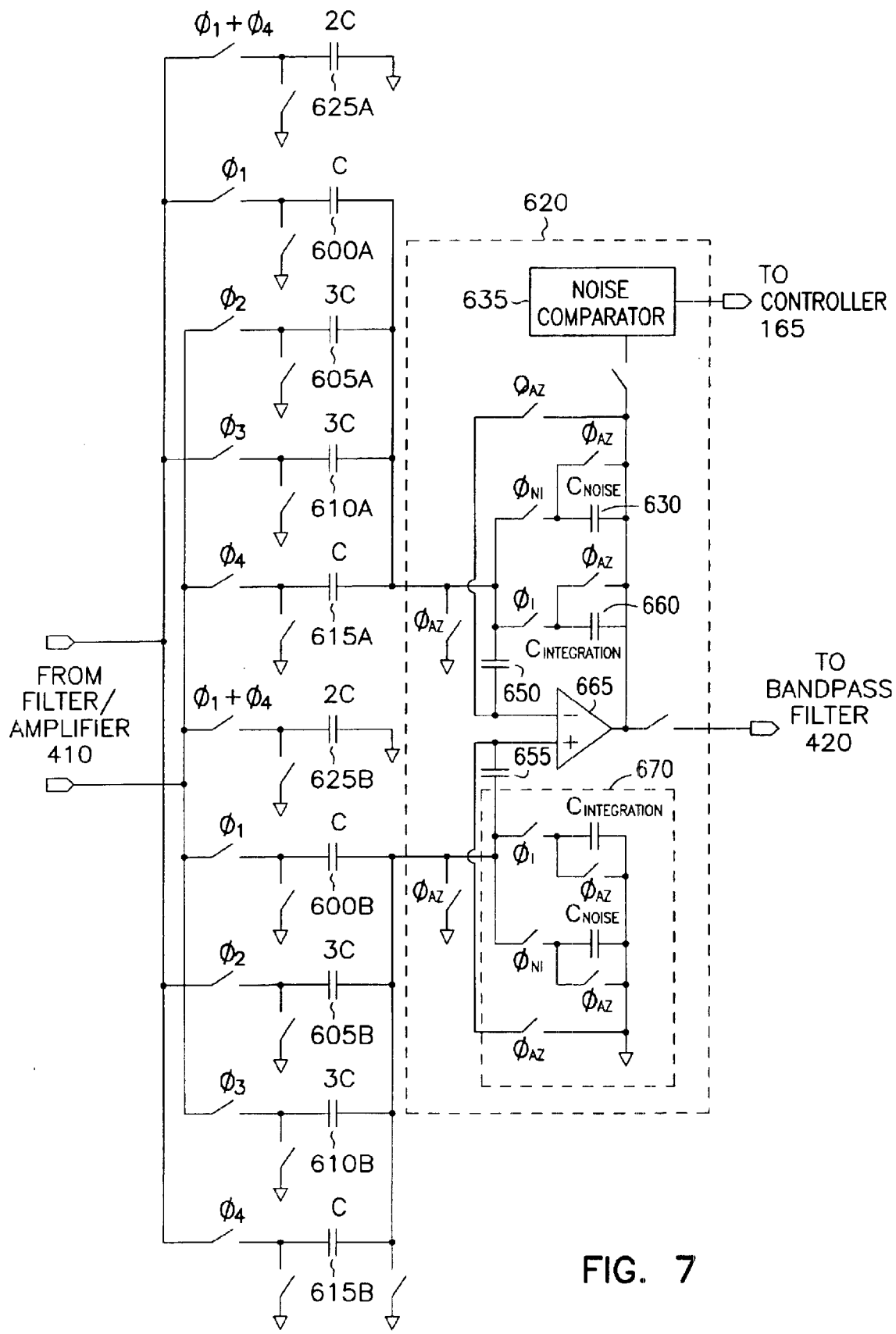
FIG. 7 is a schematic diagram illustrating one embodiment of a demodulator.

FIG. 7 is a schematic diagram illustrating one embodiment of a switched-capacitor analog demodulator 415. The output signal from preamplifier 410 is sampled onto capacitors 600A–B in response to current pulse 301, onto capacitors 605A–B in response to current pulse 302, onto capacitors 610A–B in response to current pulse 303, and onto capacitors 615A–B in response to current pulse 304. Sampling onto the capacitors is effected by closure of solid-state sampling switches in response to switch-closure inputs $\emptyset_1$ through $\emptyset_4$ that correspond to the phase of the excitation current waveform during which the switch is closed, 301 through 304, respectively. The switch-closure inputs are generated, for example, by a clock circuit synchronized with the exciter 150. Capacitors 605A–B and 610A–B provide 3 times the capacitance value of capacitors 600A–B and 615A–B, in order to provide the above-described weighting of the samples. After the weighted sampling of the output of preamplifier 410 in response to the four current pulses 301–304, these weighted samples are summed by switched-capacitor integrator 620 (also referred to as a summer).

Also shown in FIG. 7 are dummy capacitors 625A–B. Each of dummy capacitors 625A–B has a capacitance value that is twice that of one of capacitors 600A–B, and twice that of one of capacitors 615A–B. Dummy capacitors 625A–B are switched in during sample of current pulses 301 and 304. As a result, demodulator 415 presents the same load capacitance to preamplifier 410 during sampling of each of the four current pulses 301–304. As seen in FIG. 7, however, the charge that is sampled onto dummy capacitors 625A–B is not included in the weighted sample (i.e., the resulting charge is not included in the integration provided by integrator 620). Furthermore, it is understood that, in one embodiment, the capacitors shown in FIG. 7 are initialized (e.g., discharged) prior to sampling any particular sequence of current pulses 301–304.

Integrator 620 also includes input capacitors 650 and 655, which are autozeroed by switches, as illustrated, during the clock phase $\phi_{AZ}$. An integration capacitor 660, which is in the feedback path around operational amplifier 665, sums the weighted samples obtained in response to the four current pulses 301–304 during an integration clock phase $\phi_I$. A noise sampling/integration capacitor 630, which is also in the feedback path around operational amplifier 665, may be used instead to sum the weighted samples obtained in the absence of delivered current pulses during a noise integration clock phase $\phi_{NI}$, as described below. Integrator 620 also provides a matching network 670 on the other input of operational amplifier 665 for matching the above-described switched capacitor operation.

Analog-to-Digital (A/D) Converter

A/D converter 425 receives the output signal of demodulator 415 and provides a resulting digitized output signal to high pass filter 430 of digital signal processing circuit 405. In one embodiment, A/D converter 425 is implemented as an 8-bit, successive approximation type switched-capacitor A/D converter having an input range of approximately 1 Volt. According to one aspect of the invention, A/D converter 425 provides one 8-bit digital word corresponding to each sequence of four current pulses 301–304 delivered by exciter 150. Many different implementations of A/D converter 425 will be suitable for use in the present invention, including different A/D converter resolutions.

Digital Signal Processing Circuit

The digital processing circuit filters the high pass-filtered and demodulated voltage sense signal samples into the ventilation band to derive a ventilation signal. Such filtering may be accomplished by a bandpass filter or a combination of high pass and low pass filters as shown in FIGS. 6A and 6B. In one particular embodiment, high pass filter 430 is a single-pole infinite impulse response (IIR) digital filter that receives the 8-bit digital output signal from A/D converter 425, removing frequency components below its high pass cutoff frequency of approximately 0.1 Hz. Many other different embodiments of high pass filter 430 would also be suitable. High pass filter 430 advantageously further attenuates not only baseline dc components of the transthoracic impedance but also any dc offset voltages created by A/D converter 425. The output of high pass filter 430 is provided to low pass filter 435. Low pass filter 435 receives the output signal of high pass filter 430 and attenuates frequency components of the signal that exceed the low pass cutoff frequency of low pass filter 435. The signal components attenuated by the low pass filter 435 include the cardiac stroke signal, resulting from changes in blood volume in heart 115 as it contracts during each cardiac cycle.

3. Adaptive Low Pass Filter

It is only changes in the impedance signal with time that are reflective of movement of air into and out of the lungs. As stated above, therefore, a high pass filter 430 is used to remove the DC component of the impedance signal, ideally leaving only the time-varying portion of the impedance signal from which can be derived the ventilation signal used to calculate the minute ventilation. Respiratory patterns, however, vary from individual to individual, and may even vary from time to time in the same individual. This means that the peak-to-peak amplitude variations of the impedance signal may vary quite widely, which increases the dynamic range over which the minute ventilation sensor must operate and can adversely affect the accuracy of the final minute ventilation calculation.

The dynamic range problem just described can be ameliorated by implementing the filter 430 digitally as an adaptive single-pole infinite impulse response (IIR) digital filter with a variable pole frequency. The pole frequency of the adaptive high pass filter 430 can then be adjusted in accordance with the variability of the impedance signal that is input to the filter. In one embodiment, additional circuitry is implemented in the digital signal processor for continually monitoring the amplitude variations of the impedance signal and generating a signal variation parameter. The signal variation parameter is based on a specified number stored impedance signal samples may be calculated as, for example, a variance, a standard deviation, or any statistic reflecting the variability of the signal samples. If the amplitude variations of the impedance signal show a sustained increase or decrease from a defined nominal amplitude variation, the pole frequency of the high pass filter and/or other filter parameters affecting the frequency response of the filter are then adjusted in a manner that tends to decrease or increase, respectively, the amplitude variations. The filter adjustment thus nominalizes the impedance signal which places less demand upon the dynamic range of the minute ventilation calculation circuitry. Since no filtering is ideal, increasing or decreasing the pole frequency affects how much of the low-frequency time-varying components of the impedance signal are lost when it is filtered by the filter 430. In the case where the amplitude variations of the impedance signal are low compared with the nominal variation, decreasing the pole frequency of high pass filter 430 decreases the amount of time-varying signal loss and hence increases the amplitude variations of the filtered signal toward the nominal variation. Conversely, in the case where the amplitude variations are high compared with the nominal variation, increasing the pole frequency increases the amount of time-varying signal loss so that the amplitude variations of the filtered signal are decreased toward the nominal variation. The allowable variation on the high pass filter pole frequency can be determined by the maximum and minimum response times to changes in the DC impedance level. Nominalizing the time-varying component of the impedance signal in this manner improves the accuracy of the minute ventilation sensor across a wide range of impedance signal amplitude variations and simplifies processing by allowing the size of signal data to be more nearly of a predetermined size. Trending of the pole frequency used by the sensor could also be used to indicate periods of increased or decreased activity as part of a lifestyle monitoring system.

A minute ventilation sensing device for practicing the invention thus includes circuitry (e.g., code executable by the controller) for calculating a signal variation parameter from a set of impedance signal samples and circuitry for adjusting the frequency response of the high pass filter in a manner that tends to compensate for changes in the calculated signal variation parameter as compared with a specified nominal value. Such a device may be incorporated into a cardiac rhythm management device such as illustrated in FIG. 1 where the frequency response of the high pass filter may be adjusted continuously or periodically based upon changes in the signal variation parameter as calculated from impedance signal samples collected and stored on a continuous or periodic basis, respectively.

Figure 8:
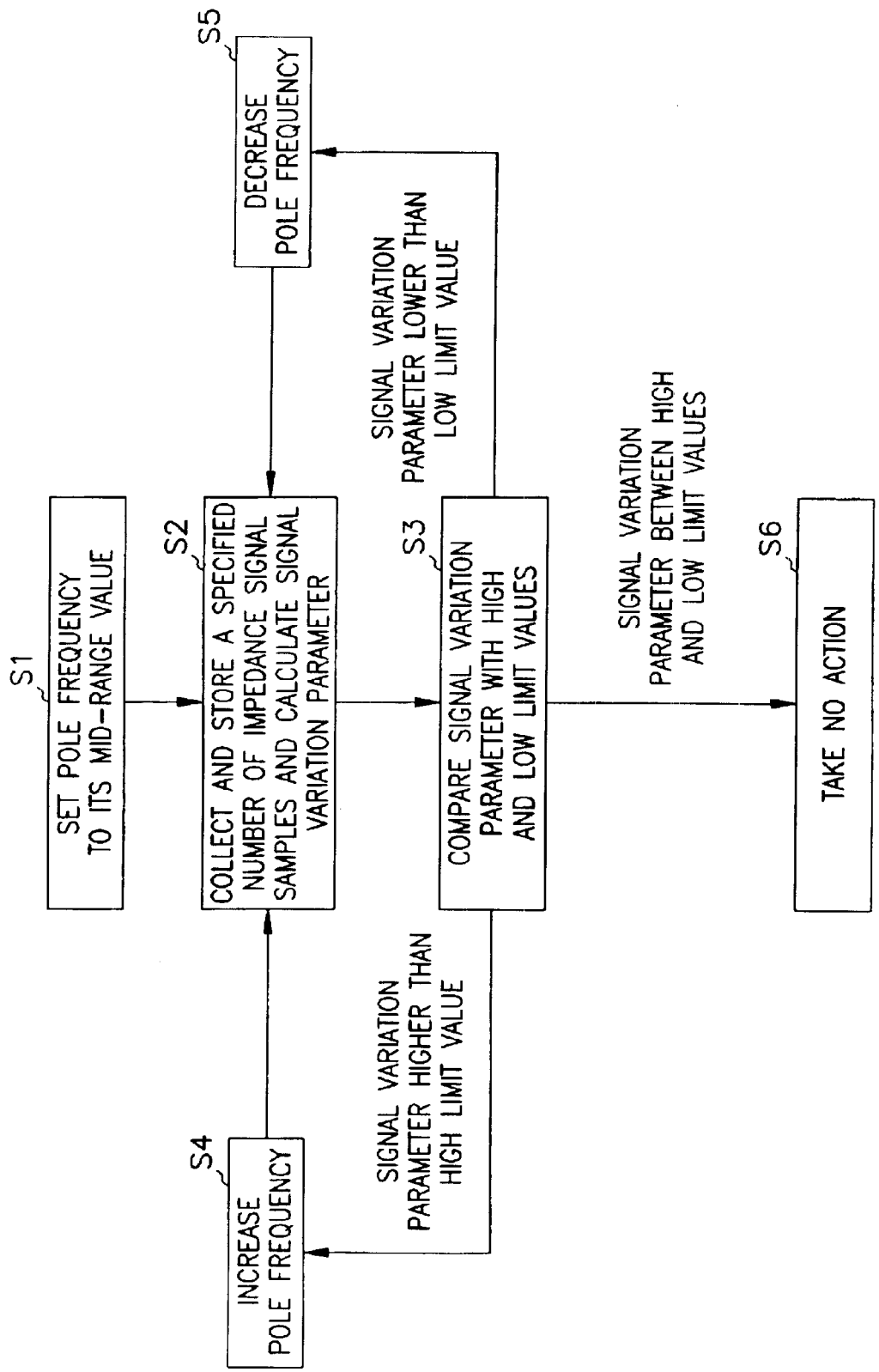
FIG. 8 is a flowchart of an exemplary algorithm for adjusting the pole frequency of a high pass filter in accordance with a calculated signal variation parameter.

FIG. 8 shows a flowchart of an exemplary implementation of the method just described as could be performed by the controller and/or digital signal processor of the device illustrated in FIG. 1. At step S1, the device begins operation by setting the pole frequency of the high pass filter 430 to its mid-range value. At step S2, the device collects and stores a defined number of samples of the impedance signal and calculates a signal variation parameter from the samples. At step S3, the calculated signal variation parameter is compared with high and low limit values each representing specified percentages of the sensor's dynamic range. If the signal variation parameter is higher than the high limit value, the pole frequency is increased at step S4, and the algorithm returns to step S2. If the signal variation parameter is lower than the low limit value, the pole frequency is decreased at step S5, and the algorithm returns to step S2. If the signal variation parameter is between the high and low limit values, no action is taken at step S6 as the impedance signal variation is deemed to be within the optimum dynamic range of the sensor. The sensor output is thus deemed valid.

In one embodiment, normal operation of the sensor may be periodically interrupted while the device performs the algorithm illustrated in FIG. 8 to adjust the pole frequency of the high pass filter on an intermittent basis. That is, rate-adaptive pacing in accordance with the calculated minute ventilation is ceased so that paces are delivered at a rate determined by programmed settings only while the signal variation parameter is calculated. Once step S6 is reached, normal operation of the sensor in calculating minute ventilation for rate-adaptive pacing is either begun or resumed. In another embodiment, normal sensor operation continues while the algorithm is executed concurrently. In either embodiment, if a situation arises where a maximum or minimum pole frequency is reached and the signal variation parameter is still above or below the high or low limit value, the device may be programmed to either cease minute ventilation sensing until the signal variation parameter comes within the desired range or take other appropriate action.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A minute ventilation sensing device, comprising:
   excitation current electrodes for imposing a current field in the thoracic cavity;
   an exciter for supplying excitation current between the excitation current electrodes;
   voltage sense electrodes for generating an impedance signal corresponding to a potential difference between two points in the thoracic cavity when the excitation current is applied;
   sampling circuitry for sampling the impedance signal;
   circuitry for filtering the impedance signal samples into a ventilation band to thereby generate a ventilation signal, wherein the filtering circuitry includes a high pass filter with a variable pole frequency for removing a DC component from the impedance signal samples;
   circuitry for calculating a signal variation parameter from a set of impedance signal samples;
   circuitry for adjusting a frequency response of the high pass filter to compensate for changes in the calculated signal variation parameter; and,
   circuitry for deriving a signal proportional to minute ventilation from the ventilation signal.

2. The device of claim 1 wherein the circuitry for adjusting the frequency response of the high pass filter increases the pole frequency of the high pass filter if the calculated signal variation parameter is higher than a specified nominal value, and decreases the pole frequency of the high pass filter if the calculated signal variation parameter is lower than a specified nominal value.

3. The device of claim 1 wherein the circuitry for adjusting the frequency response of the high pass filter increases the pole frequency of the high pass filter if the calculated signal variation parameter is higher than a specified high limit value, and decreases the pole frequency of the high pass filter if the calculated signal variation parameter is lower than a specified low limit value.

4. The device of claim 1 wherein the signal variation parameter is a variance.

5. A cardiac rhythm management device, comprising:
   a sensing channel for detecting intrinsic cardiac activity;
   a pacing channel for pacing the heart;
   a controller for delivering paces in accordance with a programmed mode;
   a minute ventilation sensor, comprising:
   excitation current electrodes for imposing a current field in the thoracic cavity;
   an exciter for supplying excitation current between the excitation current electrodes;
   voltage sense electrodes for generating an impedance signal corresponding to a potential difference between two points in the thoracic cavity when the excitation current is applied;
   sampling circuitry for sampling the impedance signal;
   circuitry for filtering the impedance signal samples into a ventilation band to thereby generate a ventilation signal, wherein the filtering circuitry includes a high pass filter with a variable pole frequency for removing a DC component from the impedance signal samples;
   circuitry for calculating a signal variation parameter from a set of impedance signal samples;
   circuitry for adjusting a frequency response of the high pass filter to compensate for changes in the calculated signal variation parameter;
   circuitry for deriving a signal proportional to minute ventilation from the ventilation signal; and,
   circuitry for modulating a rate at which paces are delivered by the controller in accordance with the signal proportional to minute ventilation.

6. The device of claim 5 wherein the circuitry for adjusting the frequency response of the high pass filter increases the pole frequency of the high pass filter if the calculated signal variation parameter is higher than a specified nominal value, and decreases the pole frequency of the high pass filter if the calculated signal variation parameter is lower than a specified nominal value.

7. The device of claim 5 wherein the circuitry for adjusting the frequency response of the high pass filter increases the pole frequency of the high pass filter if the calculated signal variation parameter is higher than a specified high limit value, and decreases the pole frequency of the high pass filter if the calculated signal variation parameter is lower than a specified low limit value.

8. The device of claim 7 further comprising circuitry for ceasing operation of the minute ventilation sensor if the calculated signal variation parameter is greater than the specified high limit value and the pole frequency of the high pass filter has reached a specified maximum value.

9. The device of claim 7 further comprising circuitry for ceasing operation of the minute ventilation sensor if the calculated signal variation parameter is less than the specified low limit value and the pole frequency of the high pass filter has reached a specified minimum value.

10. The device of claim 5 wherein the circuitry for adjusting the frequency response of the high pass filter adjusts the frequency response based upon changes in the signal variation parameter calculated from impedance signal samples collected and stored on a continuous basis.

11. The device of claim 5 wherein the circuitry for adjusting the frequency response of the high pass filter adjusts the frequency response periodically based upon changes in the signal variation parameter as calculated from impedance signal samples collected and stored on an intermittent basis.

12. The device of claim 11 wherein the circuitry for modulating a rate at which paces are delivered by the controller in accordance with the signal proportional to minute ventilation ceases operation while changes in the signal variation parameter are calculated.

13. A method for measuring minute ventilation, comprising:

imposing an excitation current field in the thoracic cavity;

generating an impedance signal corresponding to a potential difference between two points in the thoracic cavity when the excitation current field is imposed;

sampling the impedance signal;

filtering the impedance signal samples into a ventilation band to thereby generate a ventilation signal, including high pass filtering the impedance signal samples with a high pass filter having a variable pole frequency for removing a DC component from the impedance signal samples;

calculating a signal variation parameter from a set of impedance signal samples;

adjusting a frequency response of the high pass filter step to compensate for changes in the calculated signal variation parameter; and, deriving a signal proportional to minute ventilation from the ventilation signal.

14. The method of claim 13 wherein the frequency response of the high pass filter is adjusted by increasing the pole frequency of the high pass filter if the calculated signal variation parameter is higher than a specified nominal value, and decreasing the pole frequency of the high pass filter if the calculated signal variation parameter is lower than a specified nominal value.

15. The method of claim 13 wherein the frequency response of the high pass filter is adjusted by increasing the pole frequency of the high pass filter if the calculated signal variation parameter is higher than a specified high limit value, and decreasing the pole frequency of the high pass filter if the calculated signal variation parameter is lower than a specified low limit value.

16. The method of claim 13 wherein the signal variation parameter is a variance.

17. A minute ventilation sensor, comprising:

means for imposing an excitation current field in the thoracic cavity;

means for generating an impedance signal corresponding to a potential difference between two points in the thoracic cavity when the excitation current field is imposed;

means for sampling the impedance signal;

means for filtering the impedance signal samples into a ventilation band to thereby generate a ventilation signal, including high pass filtering the impedance signal samples with a high pass filter having a variable pole frequency for removing a DC component from the impedance signal samples;

means for calculating a signal variation parameter from a set of impedance signal samples;

means for adjusting a frequency response of the high pass filter step to compensate for changes in the calculated signal variation parameter; and, means for deriving a signal proportional to minute ventilation from the ventilation signal.

18. The device of claim 17 wherein the high pass filter frequency response adjusting means increases the pole frequency of the high pass filter if the calculated signal variation parameter is higher than a specified nominal value, and decreases the pole frequency of the high pass filter if the calculated signal variation parameter is lower than a specified nominal value.

19. The device of claim 17 wherein the high pass filter frequency response adjusting means increases the pole frequency of the high pass filter if the calculated signal variation parameter is higher than a specified high limit value, and decreases the pole frequency of the high pass filter if the calculated signal variation parameter is lower than a specified low limit value.

20. The device of claim 17 wherein the signal variation parameter is a variance.

* * * * *